United States Patent [19]

Yen

[11] Patent Number: 5,069,936
[45] Date of Patent: Dec. 3, 1991

[54] MANUFACTURING PROTEIN MICROSPHERES

[76] Inventor: Richard C. K. Yen, 4261 Chase Ave., Los Angeles, Calif. 90066

[21] Appl. No.: 390,628

[22] Filed: Aug. 7, 1989

Related U.S. Application Data

[63] Continuation-in-part of Ser. No. 66,811, Jun. 25, 1987, abandoned, which is a continuation-in-part of Ser. No. 351,030, Feb. 22, 1982, abandoned.

[51] Int. Cl.$^5$ .................... A61K 9/26; A61K 9/64; B01J 13/08; B01J 13/20
[52] U.S. Cl. .................... 427/213.33; 264/4.1; 264/4.3; 424/1.1; 424/7.1; 424/484; 424/491; 428/402.2; 428/402.24; 514/6; 514/885; 514/965; 935/54
[58] Field of Search .................... 264/4.1, 4.3; 427/213.33; 428/402.2, 402.24; 424/491; 514/965

[56] References Cited

U.S. PATENT DOCUMENTS

| | | | |
|---|---|---|---|
| 3,540,532 | 11/1970 | Davis, Jr. et al. | 252/8.554 X |
| 3,663,685 | 5/1972 | Evans | 424/1.1 |
| 4,107,288 | 8/1978 | Oppenheim et al. | 264/4.3 X |
| 4,269,821 | 5/1981 | Kreuter et al. | 424/81 X |

OTHER PUBLICATIONS

Martodam et al., "Albumin Microspheres as Carrier . . . ", *Proc. Natl. Acad. Sci. U.S.A.*, 76 (1979) pp. 2128-2132.

Widder et al.: "Magnetically Responsive Microspheres . . . ", *Advances in Pharmacology and Chemotheraphy*, vol. 16 (1979) pp. 213-271.

*Primary Examiner*—Richard D. Lovering
*Attorney, Agent, or Firm*—Lyon & Lyon

[57] ABSTRACT

Processes for producing biocompatible and biodegradable protein microspheres with controlled porosity and microsphere sizes are disclosed. Generally, the processes are accomplished as follows: (a) dissolving a source of protein in a mildly acidic or basic aqueous medium, in the presence or absence of a biomodifying agent, (b) adding a cross-linking reagent to the dissolved protein molecules in an amount effective subsequently to cross-link the protein molecules without gelation; (c) adding a water soluble surfactant to modify the surface of the partially cross-linked protein molecules, (d) adding a water soluble organic desolubilizer to desolubilize the protein molecules to allow cross-linkage of nearby protein molecules into water-insoluble microspheres. Alternatively, the cross-linking step of (b) is employed after desolvation of the microspheres. Incorporation of the biomodifying agent, if any, can be achieved by prior bonding to the protein molecules, addition during the formation of microspheres, or addition after the formation of the irreversible and stable microspheres. The microspheres produced by said processes are also disclosed.

24 Claims, No Drawings

MANUFACTURING PROTEIN MICROSPHERES

This application is a continuation-in-part of application Ser. No. 066,811 filed June 25, 1987, now abandoned, which is a continuation-in-part of application Ser. No. 351,030 filed Feb. 22, 1982, now abandoned.

BACKGROUND OF THE INVENTION

1. Field of the Invention

The field of this invention concerns protein microspheres, such as are useful in biological treatments, experiments, and analyses, both in vivo and in vitro, and more particularly with remarkably versatile microspheres produced by a novel method.

The method and product are widely adaptable to use with numerous chemical and biochemical agents, and their derivatives, e.g. in carrying chemotherapeutic agents, alkaloids, halogenated compounds, hormones, lipids, nucleotides, porphyrins, steroids, vitamins, lectins, metals, their oxides, chlorides or sulfides, antibacterial and antifungal agents, enzymes, and like biologically useful agents, for example oxygen carrying molecules, into a host body for specific application at the point of need. The application is enabled selectively and controllably, without side effects resultant from excessive dosage or misdirection. A chemotherapeutic agent, for example, can be carried in a manner to bypass healthy cell areas, and therefore causing less side effects and at the same time enhancing therapeutic effectiveness. In certain cases, the agent may be released slowly and continuously, or may be released rapidly in the area to be treated. The biomodifying agents do not suffer any decrease in their effectiveness. The microspheres act to transport the various agents and may modify the kinetics of release of such agents.

The microspheres are both biocompatible and biodegradable, so that undesired foreign accumulations in the host body are avoided. Moreover, the method of microsphere production utilizes primarily ambient temperatures (although heating can be used if desired). The process does not require cooking of the albumin or any other destructive process. Through cooking or other heating, the incorporated agent may be damaged and suffer reduced effectiveness.

In particular, the invention relates to novel, improved protein microspheres of very small, very uniform particle size, and with great consistency and predictability, all with reagents and materials affording a clean, biocompatible and biodegradable microsphere product. The products of the method enable in vivo application of a wide variety of attached or incorporated chemical agents, without loss of their specific functions on a controlled, sustained release and/or selective, targeted basis, while the very small, uniform particle size enables passage through even capillaries to targeted areas. Being both biocompatible and biodegradable, the products of the method are powerful tools for pin-point implementation of therapies and treatments heretofore possible only theoretically or with undesired concomitant side effects.

2. Description of the Prior Art

Protein microspheres have been produced by the emulsification of an aqueous solution of a suitable protein, e.g. human serum albumin. See, Albumin microspheres as carrier of an inhibitor of leukocyte elastase: Potential therapeutic agent for emphysema, R. R. Martodam, et al., *Proc. Nat'l Acad. Sci. U.S.A.*, Vol. 76, No. 5, pp. 2128–2132, May 1979. See also: Magnetically Responsive Microspheres and Other Carriers for the Biophysical Targeting of Antitumor Agents, K. J. Widder et al., *Advances in Pharmacology and Chemotherapy*, Vol. 16, pp. 213–271, especially pages 233–239.

As will be apparent from a consideration of the latter of the foregoing articles, albumin microspheres have been prepared by emulsifying water solutions of human serum albumin in cottonseed oil, followed by stabilization with heat which is highly disadvantageous in at least two respects: (1) the albumin becomes highly denatured and thus is recognized by the host body as foreign and is therefore rapidly eliminated; and (2) where heat sensitive chemicals are used, the agent is destroyed during the heating process. In addition, the process requires the subsequent extraction of the oil by ether washing, and sieving to classify as to size.

The concept of forming microspheres is also disclosed and claimed in U.S. Pat. No. 4,107,288 issued on Aug. 15, 1978 to Oppenheim et al. for "Injectable Compositions, Nanoparticles Useful Therein, And Process Of Manufacturing Same" ("Oppenheim"). However, the process disclosed and claimed in Oppenheim produces an aggregation of particles and further requires the process to be carried out at elevated temperatures which can denature the albumin and/or destroy heat sensitive chemicals. The problem with the Oppenheim process is that proceeding from the dissolving step directly to the step where the desolvating agent is added produces an uncontrolled reaction where the particles lump together too fast and an aggregation occurs. This is apparent from Column 3, lines 40 to 50 of the Oppenheim patent. If the aggregation formed is too clumpy, then alcohol must be added to reverse the desolvation. The Oppenheim method may be satisfactory with gelatin compounds but with albumin which is not as thick and viscous as gelatin the result with the Oppenheim process is uncontrolled aggregation when the dissolving step is immediately followed by addition of the desolvating agent.

A suitable surfactant must be employed to result in monodispersed microspheres with less than 0.1% aggregates. The critical difference between this invention and that of Oppenheim is the discovery that a suitable surfactant or detergent must be used to prepare the surface of the protein cross-linking agent complex for microsphere formation. Oppenheim teaches that the nature of the surfactant or suspending agent is not critical except that the surfactant or suspending agent should remain in solution throughout the process (column 4, line 25 to 27). The use of surfactant is not mentioned in his examples 1, 2, 3, 4, 5, 6, 7 or 8. The products were comprised of aggregated spherical particles (column 6, line 5). It is not clear if each sphere is about 330–660 nanometers in diameter, while the entire aggregate can be millimeter (thousands of microns in size) in diameter as I have found. Oppenheim's example 9 mentions "a suitable concentration of surfactant: 0.5 to 3.0% w/v (column 6, line 38). However neither the identity of the surfactant nor its importance is identified. Therefore, Oppenheim teaches away from the importance of the surfactant.

Accordingly, a significant need exists for a process by which microspheres can be created in a controlled reaction to thereby avoid aggregation and further permit uniform homogeneous microspheres to be formed which can be used with albumin and other compounds which are not as viscous as gelatin.

In addition, there is also a need for microsphere preparations with controlled porosity of the microspheres. In certain conditions, biological molecules to be deployed to the host would require protection from destructive mechanisms of the host. Protection can be afforded by a porous matrix of the microsphere, with the biological molecule, such as hemoglobin, to be covalently bonded to the interior of the microsphere. This requires that the relatively large biological molecule be able to penetrate the surface of the microspheres, which is dependent on the sizes of the pores on the surface and interior of the microspheres. One theoretical approach to incorporate such molecules in the interior of the microspheres would be to link the biological molecule to the protein molecules before the formation of microspheres. Such an approach would presume a random distribution of the biological molecule such that a majority of the biological molecules will result in the interior of the microspheres. Such may not always be the case if a biological molecule is highly hydrophilic, or is so bulky as to interfere with the formation of microspheres which in the absence of such biological molecules may be easily and controllably assembled. More importantly, the conditions used to produce microspheres may be detrimental to the biological stability and therefore to the function of the biological molecule. For example, the use of a high concentration of ammonium sulfate solution in Oppenheim's approach will certainly destroy the hemoglobin portion of any preformed hemoglobin-gelatin complex.

The primary embodiment of my methodology allows a low concentration of cross-linking agent to lightly cross-link protein molecules before their desolvation in the presence of a suitable surfactant. The sizes of the microspheres as well as the porosity of the microspheres formed is large when the concentration of cross-linking agent used is low. This is due to a lower number of internal bonds formed under well defined and easily controllable conditions.

A modification of Oppenheim's approach may also be theoretically entertained, namely that cross-linking agents may be added to the gelatin in their example before the step of "desolvation region", thus achieving a procedure similar to my invention. However, Oppenheim clearly indicates that the desolvation region can easily be overshot which will lead to uncontrolled clumping and which requires the addition of a reversal agent. If Oppenheim attempted pre-linkage of gelatin molecules, once the desolvation region is overshot, the cross-linkage of the gelatin in the presence of the cross-linking agent will prevent reversal of the condition, resulting in a highly clumped useless preparation. Furthermore, Oppenheim teaches away from the importance of a suitable surfactant, which mainly accounts for the labile condition of the "desolvation region."

My approach allows the use of a range of low concentration of cross-linking material; easily controlled duration of interaction between the cross-linking agent and the protein molecules to achieve partial and light initial cross-linkage; stability of such protein cross-linkage agent complexes; and more importantly, stabilization of microspheres by the presence of a suitable surfactant before the addition of the desolvating agent. Thus we control the sizes of the microspheres, the distribution of sizes of microspheres, and the porosity of the resultant microspheres, all of which properties are important to the specific task of carrying certain relatively large and easily biodegradable biological molecules.

In another embodiment of my process, I formed reversible microspheres by addition of a desolvation agent to unlinked protein molecules in the presence of a suitable surfactant. Subsequently, a low concentration of cross-linking agent is used to gently and irreversibly form internal bonding within the microspheres. Although superficially this embodiment may appear to resemble that of Oppenheim's approach, my method will result in well controlled microsphere sizes as well as porosity, again by virtue of the absence of an unstable "desolvation region" with the associated disadvantages discussed above.

SUMMARY OF THE INVENTION

The present invention relates to a process for producing microspheres under a controlled reaction so that the microspheres will not aggregate and form clumps.

It has been discovered, according to the present invention, that a critical step in the production of microspheres is to add a surfactant or detergent after the protein molecules have been dissolved in the solution and before the desolvating agent is added. This step is critical because the surfactant interacts with the surface of the protein molecules so that when the hydrophilicity or the ionic strength of the surrounding medium is changed, such as by addition of the desolvating agent, the individual protein molecules can come together in such a way that they have the hydrophilic regions facing the aqueous medium and hydrophobic regions in the interior of the sphere. As a result, a spherical particle is formed. In addition, the surface property of the spheres is such that it discourages aggregation between spheres to form larger clumps. When a desolvating agent is subsequently added, a controlled formation of microspheres results because the surfactant or detergent has caused the water seeking portions of the molecules to be on the outside of the protein particles. The presence of a suitable surfactant therefore allows the arrangement of individual protein molecules in such a way that they form into controlled groups of microspheres of uniform size and shape. Without this critical step, when the desolvating agent is added (as in Oppenheim) instead of the molecules being pushed together into uniform spheres they are pushed together into an aggregate of uncontrollable size and shape.

It has also been discovered, according to the present invention, that the dissolving of proteins and the use of a surfactant or detergent in our procedures enables the reaction to take place at room temperature and does not require heating.

It has further been discovered, according to the present invention, that the process can be created in two alternative sequences. In a first sequence the steps require: (a) dissolving the protein molecules at room temperature (these can be dissolved by heating as well but this has associated problems previously discussed) (b) adding a cross-linking agent such as an aldehyde to link part of the protein molecules together before they are pushed together for further cross-linkage. This provides the advantage of having more flexibility in that (i) lower concentrations of cross-linking agents can be used, (ii) the products of the reaction is relatively stable, (iii) subsequent steps can be initiated with more control, (iv) the ultimate yield can be better controlled and (v) the size of the particles can be better controlled; (c) adding the surfactant or detergent to interact with the surface of the proteins in such a way that when a desolvating agent is subsequently added, the formation of aggregates is avoided; (d) adding the desolvating agent to push the particles together into the microspheres. Since the cross-linking agent is added before any formation of microspheres, this approach is called the "pre-link" approach.

In the alternative process the steps involved are: (a) dissolving the protein molecules at room temperature (or heating) (b) adding the surfactant or detergent to interact with the surface of the proteins; (c) adding the desolvating agent to push the proteins together in a controlled manner to form microspheres; and (d) adding the cross-linking agent to bind the microspheres. This approach may be called the "post-link" approach. Since microspheres are already present when the cross-linking agent is added, this procedure will result not only in bonding of protein molecules within a single microsphere (internal bonding) but will also lead to linkage between microspheres (inter-spheric bonding). Although inter-spheric linkage can be minimized by using lower concentrations of cross-linking agent, any such aggregate formation will result in an inferior product. In addition, the yield of microspheres from the protein solution is not as optimal as in the previous process. Although both processes produce microspheres which are satisfactory, the "pre-link" approach is preferred.

The microspheres can be achieved with biological elements carried within or attached onto the microspheres by three alternative processes: (a) The microspheres can first be formed and the biological elements added thereafter. Since the microspheres produced by our process have a certain degree of porosity, the biological elements added in this manner may eventually reside on the outside or inside of the spheres, depending on the relative sizes of the biological elements and the pores, and the hydrophilicity of the biological elements. (b) Alternatively, the biological elements can be added during the process immediately prior to the addition of the desolvating agent. In this case, we expect a homogeneous distribution of the biological elements inside and on the surface of the microspheres, unless the hydrophilicity or hydrophobicity of the biological elements are such that they override a random distribution and result in preferred positions on the surface versus the interior of the spheres. (c) Finally, the proteins can have the biological elements irreversibly attached before the present invention process is started and then the process performed. The distribution of the biological elements is expected to be similar to those obtained in (b) above.

The present invention is a process for manufacturing biocompatible and biodegradable protein microspheres comprising: (a) dissolving protein molecules in an aqueous buffer solution in order to form a protein solution; (b) adding a surfactant to the solution containing protein molecules to interact with the protein molecules such that the surfactant will modify the net charge on the surface of the protein molecules; (c) adding a desolvating agent to the modified protein solution to push the modified protein molecules together in order to form the unbonded protein molecules into a stable and reversible microsphere suspension; (d) adding a cross-linking agent to the reversible microsphere suspension in order to link the protein molecules composing the microspheres together by the reactive groups on the cross-linking agent in order to form an irreversible and stable microsphere suspension. At least one biological element is then added to the irreversible microsphere suspension such that the biological element is carried by the microspheres. The biological elements can be carried inside the microspheres or on the microspheres.

The present invention also involves a process for manufacturing biocompatible and biodegradable protein microspheres which carry at least one biological element comprising: (a) dissolving protein molecules in an aqueous buffer solution in order to form a protein solution; (b) adding a cross-linking agent to the protein solution in order to link the dissolved protein molecules together by the reactive groups on the cross-linking agent; (c) adding a surfactant to the solution containing partially linked protein molecules to interact with the protein molecules such that the surfactant will modify the net charge on the surface of the protein molecules; (d) adding at least one biological element to the modified partially linked protein solution so that at least one biological element becomes attached to the protein molecules to form a protein-biological-element surfactant complex solution; and (e) adding a desolvating agent to the protein-biological-element-surfactant complex solution to push the partially linked protein molecules together in order to form internal cross-linkage and form the protein molecules into a suspension of irreversible and stable microspheres containing the at least one biological element.

The present invention further involves a process for manufacturing biocompatible and biodegradable protein microspheres which carry at least one biological element comprising: (a) dissolving protein molecules in an aqueous buffer solution in order to form a protein solution; (b) adding a surfactant to the solution containing protein molecules to interact with the protein molecules such that the surfactant will modify the net charge on the surface of the protein molecules; (c) adding at least one biological element to the modified protein solution so that the at least one biological element becomes reversibly attached to the protein molecules to form a stable and reversible protein biological element-surfactant complex solution; (d) adding a desolvating agent to the reversible protein-biological element-surfactant complex solution to push the modified protein molecules together in order to form the unbonded protein molecules into a suspension of stable and reversible microspheres carrying the at least one biological element; and (e) adding a cross-linking agent to the stable and reversible microsphere suspension in order to link the protein molecules composing the microspheres together by the reactive groups on the cross-linking agent in order to form a suspension of irreversible and stable microspheres carrying the at least one biological element.

The present invention additionally involves a process for manufacturing biocompatible and biodegradable protein microspheres which carry biological elements therein comprising: (a) providing protein molecules with at least one biological element irreversibly attached to the protein molecules to form at least one biological element carrying protein molecules; (b) dissolving the at least one biological element carrying protein molecules in an aqueous buffer solution in order to form at least one biological element carrying protein solution; (c) adding a cross-linking agent to the at least one biological element carrying protein solution in order to link the dissolved protein molecules together by the reactive groups on the cross-linking agent; (d) adding a surfactant to the solution containing partially linked at least one biological element carrying protein molecules to interact with the protein molecules such that the surfactant will modify the net charge on the surface of the biological element carrying protein molecules to form an irreversible and stable protein-biological-element-surfactant complex solution; and (e) adding a desolvating agent to the protein-biological element-surfactant complex solution to push the partially linked protein molecules together in order to form internal cross-linkage and form the protein molecules into a suspension of irreversible and stable microspheres containing the at least one biological element.

The present invention additionally involves the process for manufacturing biocompatible and biodegradable protein microspheres which carry biological elements comprising: (a) providing protein molecules with at least one biological element irreversibly attached to the protein molecules to form at least one biological element carrying protein molecules; (b) dissolving said at least one biological element carrying protein molecules in an aqueous buffer solution in order to form at least one biological element carrying protein solution; (c) adding a surfactant to the solution containing at least one biological element carrying protein molecules to interact with the protein molecules such that the surfactant will modify the net charge on the surface of the at least one biological element carrying protein molecules to form a stable and reversible protein-biological element-surfactant complex solution; (d) adding a desolvating agent to the reversible protein-biological element-surfactant complex solution to push the modified protein molecules together in order to form the unbonded protein molecules into a suspension of stable and reversible microspheres containing the at least one biological element, thereby forming a reversible microsphere suspension; and (e) adding a cross-linking agent to the stable and reversible microsphere suspension in order to link the protein molecules composing the microspheres together by the reactive groups on the cross-linking agent in order to form a suspension of irreversible and stable microspheres containing the at least one biological element.

In all the processes described above, the "at least one biological element" may be carried within the microspheres or on the microspheres, or both.

It has been discovered, according to the present invention, that in the preferred embodiment, the aqueous buffer solution is maintained between approximately 0 degrees Centigrade and 42 degrees Centigrade. Preferred buffer solutions are approximately 0.1 to 200 millimolar of potassium phosphate, potassium citrate, potassium acetate, potassium lactate, sodium phosphate, sodium citrate, sodium acetate, or sodium lactate.

It has also been discovered, according to the present invention, that the preferred pH of the aqueous buffer solution is maintained between 5 and 9.

It has further been discovered, according to the present invention, that in the preferred embodiment, the final concentration of protein molecules before addition of the desolvating agent, is 1 to 250 milligrams per milliliter of aqueous buffer solution.

It has additionally been discovered, according to the present invention, that in the preferred embodiment the protein source is composed of one or more of the following groups: albumin, collagen, hemoglobin or other members of the globin group, or immunoglobulin.

It has also been discovered, according to the present invention, that in the preferred embodiment, the amount of cross-linking agent used provides microspheres having a particle size in the approximate range of 0.01 to 5 microns. In addition, one cross-linking agent used with the present invention is a polyaldehyde in the approximate range of 0.002 to 10.0 volume per hundred volume of buffer solution. Further, the polyaldehyde is preferably chosen from the following group: glutaraldehyde, polyglutaraldehyde, or polyacrolein.

It has further been discovered, according to the present invention, that the preferred amount of surfactant added is approximately 0.1 to 50 milligrams per milliliter of buffer solution. The surfactant may be a cationic detergent. The surfactant may be an anionic detergent, such as sodium lauryl sulfate or sodium tetradecyl sulfate. The surfactant may be a non-ionic detergent, such as Nonidet-P-40, or Poloxamer 188, or any of the Tween group of detergents. Finally, the surfactant may be one of the ampholytic surfactant groups.

It has also been discovered, according to the present invention, that the preferred desolvating agent is an alcohol such methanol, ethanol, propanol, butanol, or a mixture thereof. After the processes described above have been completed, each process may involve the further step of removing the desolvating agent and all other unreacted or partially reacted soluble material by any one or more of the following processes: dialysis, filtration, centrifugation or volume dilution.

The biologic elements may be attached to the microspheres by non-covalent electrostatic attraction or by covalent bonding. If neutral drugs are already bound to the protein at the start, then the distribution is homogeneous throughout the microspheres so the drug is both inside and outside the microspheres. If the drug is highly hydrophobic, and if the drug is added during the sphere formation process, it will be entirely inside the microspheres. If the drug is very large or very hydrophilic, and if added after the formation of microspheres, then it will be on the outside of the microspheres.

If it is desired to have the drug time-released, or be protected for a period of time from destructive activities of the host, then it is preferred that the drug be on the inside of the microspheres. If it is preferred that the drug be for immediate release and also come in direct contact with the target cells (for example immunological molecules) then it is preferred that the drug be on the outside of the microspheres.

The present invention also includes the product created by separating the microspheres from the suspension produced from the aqueous solution for each of the processes set forth above. The microspheres can be removed from the suspension by various processes such as millipore tangential filtration, which is used to concentrate microspheres and remove the soluble portion of the suspension.

DETAILED DESCRIPTION OF THE PREFERRED EMBODIMENT

The present invention eliminates the complexities of prior art methods such as the contamination of oil products and denaturation of the product. In one method, the present method comprises generating a water soluble microsphere precursor by lightly cross-linking the protein molecules in solution. Then, a surfactant is added to facilitate formation of microspheres upon addition of a desolvation agent. The surfactant serves a vitally important function of preventing uncontrollable aggregation or clumping of the protein molecules in the subsequent steps. Oppenheim teaches away from this critically important step. Upon addition of the desolvation agent, the lightly cross-linked protein molecules come together to form insoluble particles visible to microscopy. During this time, the remaining active sites within the microsphere will be allowed to further complete their cross-linkage. Subsequent to completion of these reactions, the desolvation agent may be removed by washing or dialysis.

In an alternative process, the cross-linking agent is added only after the addition of the surfactant and the desolvation agent. The result provides less yield than the previous method, but still provides a working compound. The latter process also differs from Oppenheim in that the process of Oppenheim does not include the addition of the surfactant in the order presented, and this is a critical element and step of the present invention. While the use of a surfactant is discussed in Example 9 of Oppenheim, the use of a surfactant in that example is in conjunction with a highly concentrated gelatin. The steps of Example 9 of Oppenheim yield a compound with substantial aggregation (see column 6, lines 67 and 68 and Column 7, lines 1 to 2). Aggregation is unacceptable in the present invention because such aggregation will cause occlusion of small blood vessels when injected into the host body as caused by the microspheres of Widder et al. It is also important to note that use of a surfactant is never mentioned in the theoretical discussion in Oppenheim and is not recited in any of the claims. It is merely used in this one example with a highly concentrated gelatin substance.

It is therefore among the objects of the invention to provide a novel method of producing protein microspheres and an improved protein microsphere produced by the method. In addition, derivative products by the combination of the improved microspheres with a wide variety of chemical and biochemical agents having specific properties are also achieved. A result achieved is the more effective use of such agents in a host body, with biocompatibility, biodegradability and increased selective responsiveness to treatment. Such desirable effects may result from the specific particle size range and distribution of the microsphere which carried the chemical or biological agent. Alternatively, the addition of a "homing-device", such as a specific antibody, on the surface of the microspheres, containing certain biochemical agents, may enhance specific delivery of the biochemical agents to the target cells. The method of the present invention achieves a flexible control of particle size range and distribution and high productivity.

In particular embodiments of the method there is included: (1) maintaining the aqueous medium at a temperature below about 42 degrees C; (2) maintaining the pH of the aqueous medium between 5 and 9; (3) employing approximately 0.1 to 200 millimolar potassium phosphate (such as $K_2HPO_4$ or $KH_2PO_4$), sodium phosphate, sodium citrate or sodium acetate as the aqueous medium; (4) dissolving the protein in the aqueous medium, employing proteins such as serum albumin, collagen, hemoglobin or other members of the globin group, or immunoglobulin protein as the protein source; (5) using a final concentration of the protein (before addition of the desolvating agent) in the range of about 1 to 250 milligrams per milliliter; (6) employing an amount of cross-linking agent providing microspheres having a particle size in the approximate range of 0.01 to 5 micron; (7) employing a polyaldehyde as the protein molecule cross-linking agent, e.g. glutaraldehyde, polyglutaraldehyde and polyacrolein, particularly in the approximate range of 0.002 to 10.0 volume per hundred volume of buffer; and (8) adding a surfactant to facilitate microsphere formation; (9) employing suitable surfactants such as anionic detergents such as sodium lauryl sulfate and sodium tetradecyl sulfate, as well as non-ionic detergents; (10) employing an organic desolvating agent to promote formation of microspheres; (11) employing an alcohol such as ethanol as the desolvating agent.

The method further comprises carrying out protein microsphere production in the presence of other compounds adapted to be carried biocompatibly within a host body by the microspheres for treatment of the body. Alternatively, the compounds may be connected to the microspheres (e.g. covalent binding to the microsphere, or non-covalent incorporation within a relatively porous microsphere) after the formation and purification of microspheres.

For incorporating within the microsphere, there are two methods. The first method involves starting with a protein solution that already has the biochemical agents covalently bonded to the protein molecules. The covalent bond of the biochemical agents to the protein molecule can be achieved by any number of methods promoting covalent bond formation, some of which require conditions incompatible with microsphere formation. The protein-biochemical conjugates by necessity would have been purified prior to our employment for microsphere production. For example, radioactive iodine or other radioactive isotopes or dyes or hormones can bind on different sites on the albumin molecule without displacing or interfering with the binding of glutaraldehyde to such molecules, via alternative sites. Therefore, such radioactively labeled albumin molecules can still be employed in the present methodology, which employs glutaraldehyde as an internal cross-linking agent.

A variation of this method involves the addition of compounds to the unmodified protein molecules, with achievement of bonding to the protein molecules accomplished during the formation of the microspheres. Under this second method, the same cross-linking agent will effect both binding of biochemical agents to the protein molecules, as well as internal cross-linking between protein molecules. The biochemical can either (a) be added to the aqueous medium protein molecules before the addition of the cross-linking agent, or (b) be added after partial bonding of cross-linking agent with protein molecules has occurred. Under condition (a) the binding of these compounds to the albumin will compete for the same sites on the albumin molecules which are intended for internal cross-linking. Method (b) differs from (a) in that the cross-linking agent is first added to the protein solution (in the absence of the drug compound) so that sufficient numbers of sites on the albumin molecule designated for internal cross-linkage are occupied by the cross-linking agent before the drug compound is added. Method (b) then would insure adequate internal cross-linkage to occur before any interference from the drug compound, thus resulting in a more stable microsphere. Method (b) is the preferred method.

The aqueous medium is subsequently adjusted over the course of the reaction to produce microspheres. Importantly, the method includes adding a water soluble organic desolubilizer or desolvating agent to the medium in an amount effecting desolubilization of the protein molecules. In particular a liquid desolubilizer, such as an alcohol desolubilizer, e.g. methanol, ethanol, propanols, butanols or a mixture thereof is added in sufficient amount to desolubilize the protein molecules so that they form microspheres. In cases employing ethanol as the desolubilizer, a volume of ethanol up to 5 times compared with the final volume of the aqueous medium may be added to this final volume containing the protein-biochemical surfactant complex solution.

After the microspheres are produced, they are in water stable condition.

In addition to their utility as a protein source, immunoglobulins can be covalently bonded to the surface of preformed microspheres. This can be accomplished, for example, by dissolving the immunoglobulin in a suspension of the microspheres (prepared previously from immunoglobulin or other protein source, such as albumin), in the presence of a covalent linking agent such as a polyaldehyde, in covalently bonding effective amounts. This causes attaching of the immunoglobulin to the microsphere surfaces. The resulting product is useful for targeting the microsphere with or without incorporated drugs, to antigenic sites on desirable biological material, such as cells and organs.

In addition, hemoglobin may be used in conjunction with microspheres in two general approaches. The first approach involves using hemoglobin as a protein source. The methodology will be similar to that of the albumin microsphere preparation described above. However, addition of alcohol as a desolvation agent will result in conversion of hemoglobin molecules into methemoglobin molecules. Microspheres consisting of methemoglobin molecules are not useful in carrying or releasing oxygen, but are useful for radio-imaging processes such as Magnetic Resonance Imaging (MRI). For the purpose of carrying oxygen, a second approach will be as follows. Albumin microspheres are first synthesized under conditions that will result in a loosely internally cross-linked microsphere. Subsequently, these microspheres are washed to remove all denaturing agents, in particular, any residual alcohol. Then, in the presence of additional cross-linking agents, purified soluble hemoglobin will be added to the preformed microsphere suspension. The porosity of the albumin microspheres will be large enough to allow hemoglobin molecules to enter inside the microspheres and bond inside, as well as on the surface of the microspheres. This approach preserves the oxygen binding capacity of the hemoglobin molecules. In addition, when such preparation is injected to the host body, the microspheric matrix protects the hemoglobin molecules from rapid elimination, thus allowing prolonged biological function of the hemoglobin molecules.

The invention includes the products formed by the several methods enumerated, per se, and as a carrier in combination with a biomodifying compound useful in treatment of a human or animal host, i.e. a compound useful in treating conditions within the host by reduction of undesirable conditions, or enhancement of desirable conditions. The variety of useful biomodifying compound is as great as the conditions obtaining in human and animal hosts for which the biocompatible compounds are effective for treatment, and includes these classes of compounds, and particularly certain species thereof to be enumerated subsequently, as follows:

alkaloid
amino acid and polypeptides
carbohydrate
carcinogen
globulin and immunoglobulin
halogenated compound
hormone
lipid
nucleotide (including nucleosides, purine bases and pyrimidine bases)
porphyrin
steroid
vitamin
lectin
metal halide, oxide or sulfide
antibacterial compound
antifungal compound
enzyme or
chemotherapeutic agent.

Examples of biomodifying agents (or biological elements) that can be incorporated into or attached to the surface of and therefore carried by the microspheres are: a chemotherapeutic agent, such as (a) an alkylating agent (e.g. nitrogen mustard, chlorambucil, cyclophosphamide, or busulfan); or (b) an antimetabolite (e.g. methotrexate, 6- mercaptopurine, cytosine arabinoside, or 5-fluorouracil); and (c) an antibiotic (e.g. daunomycin, actinomycin-D or adriamycin); (d) a plant alkaloid (e.g. vincristine or vinblastine); (e) an adrenocorticosteroid (e.g. prednisone); (f) a steroid hormone (e.g. an estrogen, androgen or progestin); (g) an enzyme (e.g. L-asparaginase), or (h) other chemotherapeutic agent such as methylhydrazine, nitrosourea, hydroxyurea, imidazole carboxamide, procarbazine, mitotane, streptozotocin, or 5-azacytidine, and their chemotherapeutic derivatives.

Among the other biomodifying agents (or biological elements) which can be carried by the microspheres (either by being incorporated inside the microspheres or attached to the surface of the microspheres) are: (a) alkaloids such as atropine, colchicine, digitalis, ergocristine, quinine, spermine, or vinblastine; (b) amino acid compounds such as N-acetyldopamine, N-acetylglutamic acid, alanine, arginine, glycine, lysine, leucine, tyrosine, aspartylglycine or polylycine; (c) polypeptides such as insulin, hemoglobin, myoglobin and other combinations of amino acids; (d) carbohydrates such as acetobromoalphaglucose, altrose, alphaketoglutaric acid, amylopectin, 2-deoxyribose, dextran, chitosan, or aurothioglucose; (e) carcinogens such as aflatoxin, benzopyrene, N-methyl-N'-Nitro-N-Nitroso guanidine, or Nnitrosomethylurea; (f) immunoglobulins such as IgG, IgM, or autoimmune complex; (g) globulins such as hormone-binding globulins; (h) halogenated compounds such as 5-Fluorouridine or 4Fluorotryptophan or anesthetic inhalation agents such as halothane and methoxyf lurane; (i) hormones such as adrenalin, angiotensin, epinephrine, insulin, vasopressin, or follicle stimulating hormone; (j) lipids such as palmitochloride, lecithin, glutaryl coenzyme A, or phosphatidylcholine; (k) nucleotide compounds such as adenosine, $2':3'=$cyclic monophosphate, nicotinic acid, adenine dinucleotide, transfer RNA, messenger RNA or polyadenylic acid; (l) porphyrins, such as porphin, bilirubin, hemin, or hematoporphyrin; (m) steroid compounds such as cholesterol, cortisone, estrone, testosterone acetate, or androstane; (n) vitamins such as ascorbic acid, biotin, carotene, flavin mononucleotide, inositol, or niacin; (o) lectins such as concanavalin A, or phytohemoagglutinin; (p) metal compounds such as chlorides, oxides and sulfides, including $Fe_3O_4$, $ErCl_3$, aurothioglucose; (q) antibacterial or antifungal agents such as actinomycin D, ampicillin, bleomycin, chloramphenicol, cycloserine, dihydrostreptomycin, deoxyrubicin, erythromycin, gentamicin, kanamycin, neomycin, penicillin, rifamycin, streptomycin, tetracycline, or tetramycin; and (r) enzymes such as reverse transcriptase alkaline or acidic phosphatase, alcohol dehydrogenase, uricase, catalase, phosphorylase, glucose-6-phosphatase, deoxyribonuclease, endonuclease, amylase, fleuraminidase, aldolase, chondrotinase; uridine 5'-diphosphogalactase, 4-epimerase, phosphoriboisomerase, glutamine synthetase, or succinic thiokinase.

The foregoing materials, and the several exemplifications thereof, are illustrative of the biomodifying agents, or biological elements, which can be incorporated in or bound to the surface of the microsphere carriers made by the methods of the invention. In general, the microspheres function as carriers and are believed not to affect the activity of the biomodifying agent, other than for example covering the agent for selective or metered release, i.e. the biological or chemical function of the agents is unaffected, but the delivery through the body of a host is modified by incorporation or binding of the biomodifying agent to the protein microspheres.

In a highly advantageous use of the microspheres according to the invention, highly magnetic material, such as magnetite, may be incorporated in the microspheres by adding a colloidal suspension of the magnetite to the reaction mix just before desolubilization. The process enables the microspheres to be directed in vivo to areas to be treated under the influence of an externally applied magnetic field.

Applications in vitro are also contemplated, for example the separation of cell sub-populations which are useful for production of pharmaceutical compounds or cytotoxicity toward specific tumor cells. An example of such a procedure would include: (a) synthesis of a magnetic material filled microsphere; (b) attachment of immunoglobulin to the surface of these microspheres; (c) immunospecific binding of such microspheres to the desired cell sub-population; (d) separation of the desired cell sub-population in a magnetic field; and (e) elimination of microspheres by simple proteolytic digestion.

The present invention can be extended to remove unwanted matter from the body. For example, an unwanted antibody such as anti-DNA antibodies in lupus patients can be removed by filtering blood through an external filter containing microspheres coated on their surface with DNA. The anti-DNA antibody will attach to the DNA antigen and be carried away by the microspheres.

Preparation of the microspheres is carried out in a suitable vessel by: (a) dissolving a protein source in a mildly basic or acidic aqueous medium at ambient temperatures, adding a polyfunctional reagent to cross-link the protein and in a small amount so that gelation is avoided. While not wishing to be bound to any particular theory of reaction during preparation of the microspheres, it is believed that cross-linking typically does not occur at once. The polyfunctional reagent couples with sites, probably sites along the protein molecules with which some of the reactive groups on the polyfunctional reagent react, leaving the remaining sites as reactive, but as yet unreacted groups. The cross-linking agents which are unreacted extend from the much larger protein molecules, but only very limited cross-linking can occur at these conditions because of the physical separation of the protein molecules in the solution. The protein molecules are then modified by the addition of a surfactant to the aqueous medium. Following this modification, a desolubilizer is added to the solution to effect desolubilization of the protein. Since the physical distance between the pre-linked protein molecules are shortened, cross-linking occurs as the hitherto-unreacted reactive groups on one protein molecule achieve such a proximity with other protein molecules that cross-linking results. The amount of cross-linking agent to be used therefore must not be in such a high concentration so as to cause gelation of the protein solution. Subsequently microspheres are visible in the aqueous medium, ready for use with or without separation.

If desired, the biomodifying agent to be incorporated in the microsphere is added to the protein solution before the desolubilizer is added, i.e. either before cross-linking or before the desolubilization stages of the method. Alternatively, the biomodifying agent is covalently bonded to the surface of the microspheres, after microsphere formation, as explained above in connection with immunoglobulins.

The ideal microsphere suspension is one containing monodispersed microspheres of 0.05 to 0.5 microns in diameter with no aggregates present. Microspheres of greater than 0.5 microns can easily be phagocytized by macrophages in the body and removed from circulation. They also sediment easily in vitro, leading to minute clumps. Microspheres smaller than 0.05 micron remain in suspension well because of Brownian motion, but are difficult to visualize under the light microscopes for small clumps because the resolution of light microscopy under oil immersion is about 0.1 micron. However, the presence of microspheres less than even 0.05 microns can still be detected since the suspension will appear milky to the unaided eye. Both 0.5 and 0.05 micron microspheres will have no difficulty navigating through the smallest of capillary vessels which are about 7 microns in diameter.

Besides the physical properties that allow the microspheres to stay in circulation in the body, the microspheres should have the biological properties to serve their intended function. Microspheres should be made of biodegradable material so that repeated injections will not lead to toxic accumulation of the material. They should also be biocompatible with no toxicity nor immunological antigenicity which will stimulate the body to reject them and cause anaphylactic reactions on a second injection. They also should allow binding of immunoglobulins to their surfaces so that the contents of the microspheres can reach the intended cell population, with decreased side-effects for the rest of the cells in the body. If the microspheres are to carry oxygen, they must be able to bind oxygen in the lung, but release the oxygen molecules in the oxygen-starved parts of the body. If they are to carry drugs, they should be able to form covalent bonds with the drugs so that such drugs will not be prematurely released in the blood before the microspheres reach the target cell. In addition, when the target cells, such as a tumor cell, are reached, the microsphere must allow the release of the drug in sufficient quantities to kill or modify the target cell. All these requirements made the choice of starting material extremely limited. However, serum albumin, hemoglobin and fibrinogen are natural biological molecules which among others can satisfy all these requirements when formed into microspheres, to perform functions that the individual respective molecules cannot do.

Synthesis of the claimed microspheres from protein molecules is a highly critical process involving the interaction of numerous factors, all of which operate under very stringent conditions. In general:

(1) A suitable surfactant must be employed to result in monodispersed microspheres with less than 0.1% aggregates. The critical difference between this invention and that of Oppenheim is the discovery that a suitable surfactant or detergent must be used to prepare the surface of the protein cross-linking agent complex for microsphere formation. Oppenheim teaches that the nature of the surfactant or suspending agent is not critical except that the surfactant or suspending agent should remain in solution throughout the process (column 4, lines 25 to 27). The use of surfactant is not mentioned in Oppenheim's examples 1, 2, 3, 4, 5, 6, 7 or 8. The products were comprised of aggregated spherical particles (column 6, line 5). It is not clear if each sphere is about 330–660 nanometers in diameter, while the entire aggregate can be millimeter (thousands of microns in size) in diameter as I have found. Oppenheim's example 9 mentioned "a suitable concentration of surfactant: 0.5 to 3.0% w/v (column 6, line 38). However neither the identity of the surfactant nor its importance is identified. Therefore, Oppenheim teaches away from the importance of the surfactant. I have found that the identity of the surfactant is important. Also the amount used is critical. High concentrations of detergents will break up the quaternary structure of the biological molecules, rendering them inactive or prone to biological degradation. Therefore, high concentrations of detergents must be avoided. Within the acceptable range of detergent concentrations, in general, the higher concentration of detergent, the larger the microsphere. This occurs since the detergent lowers the surface tension of spherical particles and larger spheres have lower surface tension. However, when the narrow range is exceeded, the microspheres formed will not be stable and have great tendency to aggregate. In addition, such preparations will clump within minutes to form precipitates of up to centimeter sizes. When low concentrations of detergents are used, either no microspheres will form, or large precipitates will inevitably result. The timing of the addition of the surfactant may or may not be critical. I prefer to add the surfactant after the protein solution has been lightly cross-linked by the cross-linking agent so that: (1) the detergent will not interfere with any cross-linking reactions; (2) the protein molecules ar exposed for as short a time as possible to the surfactant, which in high enough concentrations will denature the protein molecules;

(2) The concentration of protein solution is important: the higher the concentration of protein material, the larger the microspheres. However, above certain critical concentrations, the protein will form gels with the cross-linking agents, rendering the subsequent steps impossible to perform. When the protein concentration is too low, microspheres do not form;

(3) The amount of cross-linking agents used and the time allowed for their interaction is also critical: too high a concentration will completely agglutinate the proteins into a gel paste; too low a concentration will not prevent formation of microsphere-looking particles, but such particles re-dissolve in water immediately when mixed with any aqueous solution. The reason for such phenomenon is due to the nature of any cross-linking agents used. By definition, cross-linking agents have two reactive sites available for binding to sites on protein molecules. Proteins, however, can have multiple binding sites. Albumin, for example, can have more than twenty binding sites per molecule. Therefore in high concentrations of protein and relatively low concentration of cross-linking agents, one protein molecule can be linked to a second protein molecule by one molecule of cross-linking agent which has one reactive site bound to one protein molecule and the other reactive site to the second protein molecule. In relatively low concentrations of protein and high concentrations of cross-linking agent, both active sites of the latter can bind to two sites on the same protein if the protein molecule is flexible enough to bend over itself for such intramolecular bonding to occur. Alternatively, in suitable concentrations of both protein and cross-linker, only one site of the cross-linking agent has time to react with a protein molecule but the second reactive site remains active, waiting for another protein molecule to come by in due time for further reaction. This condition, however, will be transient because when given enough time, even a low concentration of protein will eventually be completely cross-linked one to another or one with itself internally. Reaction mixtures containing high concentrations of both protein molecules and cross-linking agents, therefore, form gels almost instantaneously. The goal of the present invention is to have low enough concentrations of protein relative to the cross-linking agents so that most of the latter have only one site bonded to a protein molecule and have the other reactive site available, which will react after the microspheres were desolubilized from solution. Therefore it is expected that the concentration of both protein solution and the cross-linking agent, as well as the time allowed for both to interact, is critical. If all sites on the protein molecules or the cross-linking agents were used up prior to the desolubilization of the microsphere, then no reactive sites will be available for internal bond formation within the microspheres. Such microspheres, though having the same morphology of the desired microspheres, will redissolve in water or buffer when exposed to them;

(4) Drugs or other biological molecules to be carried by the microspheres may be added before the addition of the desolubilizing agent. These drugs or molecules will depend on the residual amount of totally unreacted cross-linking material available in the solution to bind them to the remaining reactive sites of the protein molecules. Alternatively, some binding sites may be available on the protein molecules through the other remaining active site of the cross-linking agent whose first reactive site has already been bonded to the protein molecule. This time period is again critical since too little time will limit the amount of drug bound and too long a time will allow too much protein-to-protein cross-linking instead of protein-to-drug bonding;

(5) A suitable desolubilizer must be used to bring the hydrophobicity vs. hydrophilicity ratio of the entire solution to a critical point where it becomes thermodynamically more stable for the protein-linker-drug complex to form microspheres instead of staying in solution. A suitable desolubilizer can be an alcohol since alcohols have hydrophilic hydroxyl groups and hydrophobic aliphatic groups in the same molecule. In general, propanols promote formation of larger microspheres than ethanol which in turn forms microspheres still larger than when methanol is used. This occurs because propanol is the most hydrophobic of the three. The amount of alcohol to be used is extremely critical. When the critical amount of alcohol to be used is exceeded, the proteins are aggregated into useless clumps, since alcohols by themselves can denature proteins. When sub-optimal amount of alcohols are used, microspheres are not formed;

(6) After the microspheres are de-solubilized from solution, a critical time is allowed for internal formation of cross-linkages so that the microspheres will not redissolve upon dialysis. This time period is critical since in certain instances, the microsphere formation will not be macroscopically evident (by the solution turning turbid or milky) immediately upon addition of the alcohol. On the other hand, prolonged time for internal cross-linkage in the presence of alcohol will lead to denaturation of the microspheres by alcohol as well as allowing microsphere-to-microsphere cross-linking as mentioned above. After this critical time period, the microspheres must be dialyzed against distilled water or suitable buffer systems to remove all traces of impurities as well as residual amounts of cross-linking agent, alcohol and unreacted substances; and (7) The use of high concentrations of salt solution for initial dialysis may lead to aggregation of certain kinds of microspheres in the dialysis bag. Only after initial dialysis in a large volume of distilled water can some microspheres be dialyzed in buffers of suitable osmolarity.

The following examples have been performed by me or under my direct supervision to prove the validity of my invention.

EXAMPLE 1

Procedure used for Formation of Hemoglobin Microspheres (1) Hemoglobin molecules were obtained by lysing packed red blood cells with three volumes of distilled water and shaking with two volumes of toluene to remove the cell membrane fragments. After sitting overnight in 4 degrees Celsius, the top layer of toluene was removed by suction. The enriched hemoglobin solution was centrifuged in a microcentrifuge at top speed for ten minutes to remove residual particular matter. Finally, the solution was filtered through a 0.2 micron filter to render the solution free from contaminating bacteria. Such solutions typically contained about 50 mg of hemoglobin per ml. solution. Further purification by gel-filtration with Sephadex 6-25 did not appear to improve the quality of microspheres substantially.

(2) Typically one volume of hemoglobin solution was reacted with one volume of glutaraldehyde of either 0.16% or 0.08% concentration for ten minutes at room temperature with no shaking after the initial thorough mixing.

(3) Then, two more volumes of sodium lauryl sulphate (SLS or SDS) of varying concentrations were added, thoroughly mixed, and allowed to react for only two minutes to avoid denaturation of the Hemoglobins. It was noted that when the concentration of SDS exceeded 2 mg/ml, hemoglobin solutions turned brown, suggestive of denaturation. The ideal concentration of SDS to use was 1.5 mg/ml. Concentrations greater than 1.8 mg/ml led to formation of small aggregates of microspheres (10 to 20% among monodispersed microspheres) Using concentrations less than 1.2 mg/ml resulted in microspheres smaller than 0.05 microns in diameter.

(4) Then, various volumes of 100% pure Ethanol were quickly and thoroughly mixed with the previously prepared solution. After this step, the solution turned turbid due to the desolubilization of microspheres from solution. Individual microspheres could now be seen under the microscope. The ideal amount was found to be about 1.50 volumes, compared to the initial volume containing the hemoglobin solution. Aggregates resulted from using 1.75 volumes of Ethanol. Microspheres of less than 0.05 microns were formed when less than 1.25 volumes of Ethanol was used.

(5) After various times of stabilization (internal crosslinkage formation within microspheres), the suspension was dialyzed against 100 volumes of distilled water first, and then normal saline to remove residual reactive agents.

(6) Of the various concentrations of reagents used, the most important ones were that of Ethanol and SDS. Not one single concentration of either reagents was found to be uniformly optimal. Monodispersed microsphere formation depended on the correct interaction of appropriate concentrations of various agents. The following table represented results from numerous experiments. More than one letter used indicates that more than one experiment was performed using the identical conditions, where the results obtained may or may not be uniform.

EXAMPLE 2

Experiments Demonstrating Criticality of Reagent Concentrations and Reaction Times for the Formation of Useful Hemispheres:

1. The Volume of Alcohol Used To Desolublized Microspheres Is Critical

| CONCENTRATION OF SDS USED MG/ML | VOLUME OF ETHANOL USED PER VOLUME OF PROTEIN SOLUTION | | | | | | | | |
|---|---|---|---|---|---|---|---|---|---|
| | 1.25 | 1.50 | 1.75 | 2.00 | 2.25 | 2.50 | 3.00 | 4.00 | 6.00 |
| 0.00 | | | | | | | E | E | |
| 0.01 | | | | | E | E | | | |
| 0.02 | | | | | E | E | | | |
| 0.03 | | | | | E | E | | | |
| 0.04 | | | | | E | E | | | |
| 0.05 | | O | | C | E | E | E | E | |
| 0.10 | | O | | C | | D | E | E | |
| 0.15 | | O | | C | E | | | | |
| 0.20 | | O | | C | | D | D | E | |
| 0.25 | | | | | | | D | E | |
| 0.30 | | O,E | E | A,E | | D | B | E | |
| 0.50 | | | | | | | D | E | |
| 0.60 | | C,C | E | E | | | | | |
| 1.00 | B,C | A,B, C,C | B,E | E | | | E | E | |
| 1.20 | C,C | A,B | | | | | | | |

-continued

| CONCENTRATION OF SDS USED MG/ML | VOLUME OF ETHANOL USED PER VOLUME OF PROTEIN SOLUTION | | | | | | | | |
|---|---|---|---|---|---|---|---|---|---|
| | 1.25 | 1.50 | 1.75 | 2.00 | 2.25 | 2.50 | 3.00 | 4.00 | 6.00 |
| 1.40 | C,C | A,B | | | | | | | |
| 1.50 | | A,A | | | | | E | E | |
| 1.60 | A,C | A,A | | | | | | | |
| 1.80 | B,C | A,B | | | | | | | |
| 2.00 | | | | | | | E | E | |
| 2.25 | | | | | | | | E | |
| 2.50 | | | | | | | | E | |
| 2.75 | | | | | | | | E | |
| 3.00 | | | | | | | | E | |
| 3.25 | | | | | | | | E | |
| 4.00 | | | | | | | | E | |
| 5.00 | | | | | | | | E | |

KEY:
"A" means 100% monodispersed microspheres of 0.05 to 0.2 microns with microaggregates or gross precipitation of microspheres.
"B" means less than 100% monodispersed microspheres of 0.05 to 0.2 microns with 10-20% microaggregates. No gross precipitates.
"C" means microspheres of less than 0.05 microns, probably 100% monodispersed.
"D" means microspheres of greater than 0.2 microns with microaggregates.
"E" means useless gross precipitations of protein aggregates.
"O" means no formation of microspheres of any size.

Significance: This experiment demonstrates:
(1) Within the acceptable range of ethanol used (e.g. 1.50 v/v), the concentration of surfactant used is important; some microaggregates are observed when SDS concentration is below 1.40 mg/ml or above 1.80 mg/ml. The ideal concentration is between 1.50 to 1.60 mg/ml.
(2) A high concentration of ethanol (greater than 1.75 volume per volume of protein solution) will inevitably cause aggregates of hemoglobin microspheres;
(3) However, a ratio of 1.25 (v/v) results usually in small spheres too difficult to handle and difficult to assess visually if clumping occurs.
(4) It is expected for each species of protein molecule and each initial concentration of protein solution, the critical concentration of ethanol and SDS to be used will vary, but will similarly be within a narrow range.

2. Critical Time for Internal Bond Formation And Stabilization

Method: One volume of hemoglobin solution (50 mg/ml) mixed with one volume of glutaraldehyde (0.08% concentration) for 10 minutes. Then two volumes of SDS (0.3 mg/ml) was added with thorough mixing and reacted for two minutes. Two volumes of Ethanol was then added. Under these conditions, the solution did not turn turbid immediately, indicating the delayed formation of microspheres. Subsequently, at different time points, an aliquot of the solution was further diluted with 1.8 volume of water to decrease the final concentration of Ethanol to prevent any denaturation by the alcohol. Then immediately, the solution was examined under 1000× microscopy to determine if microaggregates or microspheres were formed.

| TIME FOR STABILIZATION (MIN.) | APPEARANCE OF SOLUTION | RESULTS |
|---|---|---|
| 0 | clear | No microspheres |
| 10 | slightly turbid | No microspheres |
| 20 | slightly turbid | 0.1 micron microspheres, 90% monodispersed; some microaggregates |
| 25 | moderately turbid | Over 50% of microspheres form microaggregates of 5-10 microspheres each |
| 30 | fully turbid | Over 50% of microspheres form microaggregates of 5-10 microspheres each |
| 40 | fully turbid | Only useless aggregates seen |
| 50 | fully turbid | Only useless aggregates seen |

Significance: When the volume of ethanol to be used as desolvating agent relative to the initial protein solution is great, e.g., greater than 1.5, ethanol must be removed within 20 minutes by dialysis or other methods. Otherwise, additional microaggregates will be formed, rendering the preparation useless under these conditions.

EXAMPLE 3

Experiments to Demonstrate the Functionality of Microspheres: Can Hemoglobin Microspheres (Hemispheres) Bind Oxygen?

Hemispheres were prepared by the previous described method: One volume of hemoglobin (about 50 mg/ml buffer) reacted with one volume of glutaraldehyde (0.08%) for ten minutes. Then two volumes of SDS (0.3 mg/ml) was added. After two minutes, two volumes of ethanol (100%) was used to desolubilize the hemispheres from solution. Dialysis against distilled water started within one hour. These hemispheres were about 0.1 microns in diameter.

The rationale of the experiment was as follows: Oxygen dissolves in buffer and readily equilibrates with a second buffer containing a different amount of dissolved oxygen. In the absence of any oxygen-binding molecules, such as hemoglobin or oxygen-binding particles such as hemispheres, the resultant oxygen concentration will be the arithmetic mean of the two original concentrations. The same arguments apply to carbon dioxide or any other gas. The concentration of such dissolved gases are expressed as partial pressures. In the presence of oxygen-binding hemispheres, however, the buffer has more oxygen content than is apparent from the measurement of partial pressure of oxygen alone because the hemispheres serve as a reserve or reservoir whose content is related to, but not directly measurable from, instruments measuring partial pressures. When oxygen is extracted from blood, for example, the partial pressure drops less than expected because the reservoir will instantaneously release some of its bound oxygen. Most clinical laboratories measure partial pressure as a means of assessing the total oxygen content in the blood because there is a direct relationship between the oxygen partial pressure and the amount of oxygen bound to hemoglobins. If the hemispheres indeed bind oxygen reversibly, it is expected that these will work like red blood cells. Therefore, when one volume of hemisphere suspension is mixed with one volume of buffer, the partial pressure of the resultant mixture should be closer to the original partial pressure of the hemisphere than the arithmetic mean of the starting solutions. The partial pressure of carbon dioxide was used as a control to prove that the hemisphere suspension has been added to an equal volume of buffer solution.

Experiment 1: Mixing equal volumes of buffer #1 and buffer #2, both are calibration buffers for the blood gas machine and do not contain hemoglobins or hemispheres

|  | #1 Buffer | #2 Buffer | Expected Mean | Measured Pressure |
|---|---|---|---|---|
| $pO_2$ | 60 | 174 | 117 | 121 |
| $pCO_2$ | 58 | 17 | 38 | 37 |

Comment: The measured partial pressure of both oxygen and carbon dioxide are similar to the arithmetic mean as expected, since neither #1 or #2 buffer solutions contain any reservoir molecules for oxygen.

Experiment 2: Mixing Equal Volumes of Venous Blood with #2 Buffer

|  | #1 Buffer | #2 Buffer | Expected Mean | Measured Pressure |
|---|---|---|---|---|
| $pO_2$ | 86 | 174 | 130 | 106 |
| $pCO_2$ | 35 | 17 | 26 | 27 |

Comment: The measured partial pressure of $CO_2$ confirmed that equal volumes were used. Venous blood has unsaturated hemoglobin which has strong affinity for oxygen which it extracts from the #2 buffer, resulting in a partial pressure of oxygen 24 torrs lower than the arithmetic mean.

Experiment 3: Mixing Equal Volume of #1 Buffer With Hemisphere Suspension

|  | #1 Buffer | Hemispheres | Expected Mean | Measured Pressure |
|---|---|---|---|---|
| $pO_2$ | 58 | 144 | 101 | 114 |
| $PCO_2$ | 58 | 3 | 31 | 29 |

Comment: Hemispheres do bind oxygen and can release it to a relatively oxygen-poor environment (#1 buffer). If hemispheres cannot bind oxygen or bind oxygen without being able to release it, the resultant $pO_2$ of the mixture will be similar to the expected mean. The amount of hemoglobin present in the hemisphere suspension is estimated to be one-twelfth of that in the venous blood. Therefore, a difference of 13 torrs as compared to a difference of 24 torrs in experiment 2 is reasonable.

A second batch of hemispheres was prepared with modification from the above batch: One volume of hemoglobin (50 mg/ml) was reacted with glutaraldehyde (0.08%) for ten minutes after which two volumes of SDS (1.5 mg/ml) was added. After two more minutes, ethanol, only 1.5 volume instead of 2.0 volume, was added. The suspension was dialyzed within ten minutes against distilled water. The preparation was 100% monodispersed with no clumping, and with uniform size of 0.1 micron in diameter.

Since all three previous experiments were accomplished using hemisphere suspensions directly after dialysis, the question remains whether residual hemoglobin molecules left in solution was responsible for the results obtained. This batch was cleansed of hemispheres from any contaminating hemoglobins by first centrifugation at 5000 rpm for 10 minutes and subsequently re-suspending the hemispheres in phosphate buffered saline.

Experiment 4: Mixing Equal Volumes of #1 Buffer With Washed Hemispheres

|  | #1 Buffer | Hemispheres | Expected Mean | Measured Pressure |
|---|---|---|---|---|
| $pO_2$ | 68 | 133 | 100 | 118 |
| $pCO_2$ | 57 | 0 | 29 | 28 |

Comment: This experiment demonstrated that an 18 torr difference can still result when hemispheres were purified from soluble hemoglobin. It proved that purified hemispheres can release oxygen (which they carry) to a more oxygen-starved buffer solution.

Experiment 5: Mixing Equal Volumes of #3 Buffer With Washed Hemispheres

|  | #3 Buffer | Hemispheres | Expected Mean | Measured Pressure |
|---|---|---|---|---|
| $pO_2$ | 110 | 154 | 132 | 141 |
| $pCO_2$ | 38 | 0 | 19 | 21 |

Comment: $pO_2$ in water at atmosphere pressure equals 21% of 760 torr, i.e. 160 torr. This hemisphere preparation is almost completely saturated. Again, it released oxygen to a buffer with lower $pO_2$.

Significance: Experiments 1 to 5 demonstrate that the hemisphere preparation can bind and release oxygen to a more oxygen-deprived solution. It is expected that this preparation is able to perform a similar task when injected intravenously to a patient who, for whatever reason, is deprived of oxygen in its tissues and/or organs.

EXAMPLE 4

Procedures Used for the Formation of Albumin Microspheres and Experiments to Demonstrate the Effects of Varying Reagent Concentrations Experiment 1: The Effect of SDS Concentration on Microsphere Formation Method: One volume of HSA (80 mg/ml) was reacted with one volume of GL (0.16%) for 10 minutes and then one volume of SDS. (various concentrations) was added. After 5 minutes, a buffer was added (one volume) with thorough mixing. This step was included so that when a drug or other compounds are to be included, they may be added in this step. In a parallel experiment, a ferromagnetic suspension which was purchased from a commercial source was used. A minimum amount of ethanol was used after another 5 minutes to desolubilize microspheres. Diameters of microspheres formed were:

| CONCENTRATION OF SDS mg/ml | RESULTS Without Fe$_3$O$_4$ (control) | With Fe$_3$O$_4$ (as additive) |
| --- | --- | --- |
| 24 | 1.5 | 1.0 |
| 20 | 1.0 | 0.5 |
| 16 | 0.5 | 0.2 |
| 12 | 0.2 | 0.1 |
| 8 | 0.1 | 0.05 |
| 4 | 0.05 | <0.05 |
| 0 | gross, useless clumps | <<0.05 |

Comments: These results indicated that a surfactant is vital to the formation of useful microspheres. Higher concentrations of SDS produced larger microspheres. The ferromagnetic solution contained a surfactant that counteracted the effect of SDS, making it necessary to use even higher concentrations of SDS to achieve the same size of microspheres. The commercial source would not disclose the identity of the surfactant that was present in their preparations. This experiment demonstrates the critical contribution of surfactant (in terms of the nature and the concentration of the surfactant) to microsphere formation, in contradistinction to the teachings of Oppenheim.

Experiment 2: Effect of Time of Interaction With SDS On Microsphere Size

Prolonged exposure of protein to SDS may cause excessive denaturation. On the other hand, insufficient time for SDS interaction may result in suboptimal conditions for microspheres. Time of exposure to SDS may be critical as demonstrated below.

Method: One volume of HSA (80 mg/ml) was thoroughly mixed with one volume of GL (0.24%). After an incubation time of 15 minutes or more, two volumes of SDS (6 mg/ml) were added and incubated for various times. After a total of 40 minutes, twelve volumes of ethanol were added. Microspheres were all 100% monodisperse.

| INCUBATION TIME WITH SDS, IN MINUTES | DIAMETER OF MICROSPHERES, IN MICRONS |
| --- | --- |
| 25 | <0.1 |
| 20 | 0.1 |
| 15 | 0.1 |
| 10 | 0.3 |
| 5 | 0.1–0.3 |
| 0.2 | 0.3–0.5 |

Comment: As short an incubation time with SDS as 0.2 minutes results in good microsphere formation. Therefore, prolonged incubation with SDS is to be avoided. Addition of SDS probably interferes with interaction of GL with HSA since the latter interaction was interrupted sooner with longer SDS incubation time, resulting in small microspheres.

Experiment 3: Effect of Protein Concentration On Formation of Microspheres

The purpose of the experiment was to determine the range of protein concentrations with which an arbitrarily chosen concentration of glutaraldehyde (GL) could react with subsequent conditions suitable for microsphere formation.

Method: One volume of human serum albumin (HSA) of various concentration in 1 mM phosphate buffer (pH 7.0) was thoroughly mixed with one volume of GL (20% by vol. in water, containing also 2 mg/ml of SDS). After ten minutes, 6 vols. of ethanol (100%) was added and thoroughly mixed.

| Concentration of HSA mg/ml | Color of solution before addition of ethanol | Result |
| --- | --- | --- |
| 100 | deep yellow | Solid gel |
| 80 | deep yellow | Solid gel |
| 60 | yellow | Solid gel |
| 40 | yellow | mesh of cotton-like precipitate |
| 20 | pale yellow | mesh of cotton-like precipitate |

Comment: This initial experiment demonstrated that under these conditions, the concentration of protein as well as GL used was excessive and that as such, high concentrations of HSA were less likely to result in favorable conditions for microsphere formation.

Experiment 4: Effect of using a Lower Concentration of Cross-Linking Agent and Higher Concentrations of Surfactant Subsequent refinements demonstrated that a high concentration of HSA may be used. However, the concentrations of other reagents must be modified to adjust for a high concentration of HSA.

In another experiment, one volume of HSA (250 or 80 mg/ml) was mixed with one volume of GL (only 0.16 %) for 10 minutes. Then, one volume of SDS (at 6 or 3 mg/ml) was mixed into the mixture for 5 minutes. Then, one volume of water was added for 5 more minutes before 4.33 volumes of ethanol was thoroughly mixed into the solution. Diameter of microspheres (in microns) were:

| Concentration of HSA, mg/ml | Concentration of SDS mg/ml | | | |
| --- | --- | --- | --- | --- |
| | 2 | 3 | 4 | 6 |
| 250 | | 0.5 | | 1.0 |
| 80 | 0.05 | | 0.2 | |

Comment: As high a concentration of HSA as 250 mg/ml can still result in good microsphere formation if the other agents used were in appropriately compensated concentrations. In particular, the GL concentration used here (0.16%) was significantly lower than that used in Experiment 3 (20%). Thus, the protein molecules were only lightly cross-linked and gelation is avoided.

Experiment 5: Effects on Microsphere Formation of Using High Protein Concentrations, Low Cross-Linking Agents, and High Surfactant Concentrations, in the Presence of a Chemotherapeutic Drug Method: One volume of HSA was thoroughly mixed with one volume of a significantly lower concentration of GL (0.16%) for 10 minutes, followed by addition of one volume of SDS, at various concentrations, for 5 minutes. Subsequently, one volume of Adriamycin (1.6 mg/ml), intended as the chemotherapeutic agent to be carried by the microspheres, was added. After another 5 minutes, four volumes of ethanol (100%) was rapidly and thoroughly mixed into the solution. Microsphere suspensions were dialyzed within an hour against distilled water. Diameter of microspheres obtained were (in microns) were:

| Concentration of HSA, mg/ml | Concentration of SDS mg/ml | | | | |
|---|---|---|---|---|---|
| | 12 | 10 | 8 | 6 | 4 |
| 80 | 0.8 | 0.5 | 0.4 | 0.3 | 0.1 |
| 60 | 0.5 | 0.2 | 0.1 | 0.05 | <0.05 |
| 40 | 0.1 | 0.07 | 0.05 | <0.05 | <<0.05 |

Comment: This experiment demonstrated that microsphere size was determined by the combined effect of HSA and SDS concentrations. The presence of a chemotherapeutic agent before the addition of a desolubilizing agent did not adversely affect microsphere formation. The range of suitable HSA to use depended on the concentration of SDS used. It was again demonstrated that when a GL concentration of only 0.16% is used and reaction time is limited to 10 minutes, gelation of protein is avoided and microspheres may be produced.

Experiment 6: The Effect of Glutaraldehyde Concentration On Microsphere Formation Preliminary experiments demonstrated that the lowest initial concentration of GL that can internally cross-link microspheres so that the microspheres do not re-solubilize on dilution with buffer was about 0.04% when added to HSA solutions on a one volume-to-one volume ratio. The following experiment was performed to assess the effect of GL concentration on microsphere size:

One volume of HSA (80 mg/ml) was mixed with one volume of GL (various concentrations) for 10 minutes. Then, one volume of SDS (8 mg/ml) was mixed into the solution for 5 minutes. Subsequently, ferromagnetic colloidal solution or water was added for 5 minutes. $Fe_3O_4$ was added as a carrier marker so that when necessary, microspheres on examination under the Scanning Electron Microscope could be identified and distinguished from cellular components. (An additional purpose was to make the microspheres so prepared magnetically susceptible and migrate in a magnetic field). Then, a minimum amount of ethanol (100%) was added to desolubilize the microspheres. Dialysis commenced within one hour against distilled water. The diameter of microspheres obtained (in microns) were:

| CONCENTRATION OF GL (%) | RESULTS | |
|---|---|---|
| | Without $Fe_3O_4$ | With $Fe_3O_4$ |
| 0.36 | Precipitated, useless | Precipitated, useless |
| 0.24 | <0.01 | 0.01 |
| 0.16 | 0.1 | <0.05 |
| 0.12 | 0.1 | 0.05 |
| 0.08 | 0.2 | 0.10 |
| 0.04 | 0.6 | 0.30 |

On subsequent examination, however, microspheres prepared with less than 0.08% GL appeared to be re-solubilized upon dialysis or dilution with buffers.

Comment: The fact that microsphere sizes increase with decreased concentration of GL suggested that within the time limit of 10 minutes, a minimum concentration of GL must be used to achieve enough attachment to protein molecules which could subsequently be used for internal cross-linking upon desolubilization of such protein molecules into microspheres. As expected, an initial concentration of GL less than 0.08% results in insufficient internal bonds, leading to re-solubilization on mixing with buffer. Higher concentrations, e.g. 0.16% GL, resulted in multiple and numerous internal cross-link formation, thus forming very rigid and small microspheres. Excessively high concentrations (0.36%) of GL under these conditions resulted in useless precipitation of grossly over-cross-linked material. The commercially obtained ferromagnetic preparation of $Fe_3O_4$ contained detergents of unknown identity and effect, which obviously affected the sizes of the microspheres prepared in its presence.

Experiment 7: Effect of Prolonged Interaction of GL With HSA in Presence of Ferromagnetic Solutions Because the previous experiment demonstrated that microspheres prepared by interaction of GL with HSA for 10 minutes were exceedingly small, this experiment was designed to determine if a longer incubation or reaction time will generate stable microspheres of different sizes.

Method: One volume of HSA (80 mg/ml) was reacted with GL (various concentrations) for 15 minutes before addition of SDS (4- mg/ml). After 5 more minutes, $Fe_3O_4$ colloidal solution, purchased from a commercial source (which will not disclose the surfactant they use in this preparation), was added. After another 5 minutes, a minimum amount of ethanol needed for desolubilization was rapidly added to the solution.

| CONCENTRATION OF GL (%) | DIAMETER OF MICROSPHERES | |
|---|---|---|
| | before dialysis | after dialysis |
| 0.32 | <0.05 | <0.05 |
| 0.28 | <0.05 | <0.05 |
| 0.24 | 0.05 | 0.05 |
| 0.20 | 0.10 | 0.10 |
| 0.16 | 0.7-1.0 | 0.7-1.0 |

Comment: This experiment again demonstrates that lower concentrations of GL produced microspheres of larger sizes. The experiment also demonstrated that microspheres prepared with a minimum of 0.16% GL were stable after dialysis, which removed residual reagents. Moreover, this experiment demonstrated the importance of the interaction between various steps in the manufacture of microspheres. Whereas reaction for 10 minutes using 0.16% GL (as in Experiment 6) produced microspheres of <0.05 microns in the presence of $Fe_3O_4$ containing unknown amounts of detergent, incubation of 15 minutes (in this experiment) resulted in microspheres of 0.07 to 1.0 microns. Also, as will be demonstrated below, the higher concentration of SDS used in this experiment (4 mg/ml) was only half that of the previous experiment, and yet this combination of GL and SDS concentration produced larger microspheres, an opposite effect from the expected result from consideration of the SDS concentration alone. Further investigations as to the identity of the material species responsible for such unexpected results were not conducted since $Fe_3O_4$ solutions will not be routinely used in preparation of microspheres, and, as noted throughout, the commercial source refused to disclose such information.

Experiment 8: Effect of Addition on Biologically Active Molecules to Microsphere Formation Because microspheres were designed to be carriers of biologically active molecules, in particular drugs, the effect of the presence of drugs such as Adriamycin during the manufacture of microspheres was assessed.

Method: One volume of HSA (80 mg/ml) was reacted with one volume of GL (0.16%) for 10 minutes. Then, SDS (4 or 8 mg/ml) was added for 3 minutes. Thereafter, Adriamycin (ADR) of various concentrations was thoroughly mixed into the solution for 7 more minutes. If no precipitates were formed, a minimum amount of ethanol was added to desolubilize microspheres.

| CONCENTRATION OF ADR (MG/ML) | RESULTS WITH 4 MG/ML SDS | WITH 8 MG/ML SDS |
|---|---|---|
| 3.2 | Gross precipitates before + ethanol | Turns turbid, but no gross precipitate |
| 1.6 | Gross precipitates before + ethanol | Turns turbid, but no gross precipitate |
| 0.4 | 0.1 micron spheres, after addition of ethanol | 0.4 micron spheres, after addition of ethanol |

+ = addition of

Comment: Concentrations of ADR higher than 0.4 mg/ml apparently interfere with the formation of microspheres, which may be partially counteracted with a higher concentration of SDS (e.g. 8 mg/ml). At non-interfering concentrations of ADR, the effect of SDS concentration is as expected, that higher concentrations of the latter produced larger microspheres. Therefore, the concentration and the presence of a surfactant is critically important.

Experiment 9: Effect of Using Alcohol Other Than Ethanol

Longer chain alcohols are expected to be more hydrophobic and create an environment favorable for formation of larger microspheres.

Method: One volume of Bovine Serum Albumin was thoroughly mixed with one volume of GL for 10 minutes. Then, one volume of SDS (4 mg/ml) was added. After another 5 minutes, alcohol was added (4 volumes).

| CONC OF BSA MG/ML | CONC OF GL | ETHANOL:BUTANOL | DIAMETER IN MICRONS |
|---|---|---|---|
| 40 | 0.08% | 2:0 | 0.1 |
| 40 | 0.08% | 2:1 | 1.0 |
| 40 | 0.08% | 2:2 | 1-2 |
| 20 | 0.04% | 2:0 | 0.1 |
| 20 | 0.04% | 2:1 | 0.2 |
| 20 | 0.04% | 2:2 | 0.5 |

Comment: Bovine serum albumin can form microspheres. Increasing the hydrophobicity of the desolubilizing agent resulted in larger microspheres.

Further experiments demonstrated that Propanol could be used; however, Propanol was less desirable. One volume of HSA (80 mg/ml) added to one volume of GL (0.08%) for ten minutes was followed by 5 minutes of incubation with one volume of not more than 2.0 mg/ml SDS. Subsequently, one volume of $Fe_3O_4$ (0.4%) was added for another 5 minutes. Desolubilization with 3.4 volumes of propanol resulted in microspheres of 0.5 to 1.0 microns. Clumps of proteinase material resulted when the concentration of SDS exceeded 2.0 mg/ml.

Experiment 10: Affect of Amount of Alcohol Used On Microsphere Size

Method: One volume of HSA (40 mg/ml) was mixed thoroughly with one volume of GL (0.16%) for 15 minutes. Then, one volume of SDS (36 mg/ml or 24 mg/ml) was added for 5 minutes. Subsequently one volume of 1 millimolar phosphate buffer (pH 7.8) was added. After another 5 minutes, various amounts of ethanol (100%) were rapidly added and mixed into the solution to desolubilize microspheres.

| CONCENTRATION OF SDS, MG/ML | VOLUME OF ETHANOL/ VOLUME OF PROTEIN SOLUTION | DIAMETER OF MICROSPHERES, MICRONS |
|---|---|---|
| 36 | 10 | 0.05 |
| 36 | 12 | 0.2 |
| 36 | 14 | 0.2–0.8 |
| 36 | 16 | 0.1–1.0 |
| 24 | 10 | NOT VISIBLE |
| 24 | 12 | <<0.05 |
| 24 | 14 | 0.05–0.1 |
| 24 | 16 | 0.1 |

Comment: Due to the relatively low concentration of HSA, high concentrations of SDS were needed. Even then, at a high ethanol volume of 10, microspheres were not formed. The range of microsphere sizes was heterogeneous and, in general, larger microspheres were formed with higher ethanol volumes. It was apparent that ethanol was not as effective as SDS or HSA concentration in influencing the size of microspheres. Ethanol is used here as a desolubilizing agent. Therefore, it is expected that a higher yield of microspheres (and less protein left in soluble form) when larger amounts of ethanol were used will be obtained.

In the following examples, all parts and percentages are by volume unless otherwise noted.

EXAMPLE 5

Microsphere Preparation

To one part by volume of an aqueous medium comprising 1 mM $K_2HPO_4$ at about 25 degrees Celsius in a suitable vessel, there was added bovine serum albumin (BSA) to an initial concentration of 80 mg/ml. The BSA may in part be labeled with a tracer such as fluorescein-isothiocyanate dye or a radioisotope such as that of Iodine. One part by volume of glutaraldehyde, predissolved in another portion of the aqueous medium (0.16% v/v), was added with gentle stirring. Two parts of sodium dodecyl sulfate, pre-dissolved in a portion of the aqueous medium (8 mg/ml), were added with gentle stirring. Eight parts of ethanol/propanol (95/5) were added rapidly with gentle stirring. On standing, microspheres appear as a cloudy suspension. Chill the suspension to 4 degrees Celsius and let stand overnight. The microspheres can be centrifuged and washed with any desirable aqueous medium, or the microsphere suspension can be dialyzed against normal saline, to remove alcohol. The product microspheres are characterized by uniform, small size, 0.5 to 0.7 microns, + or −20%, a porosity enabling swelling in water and the ability to absorb and release foreign material, nearly perfect sphericity, milky whiteness in aqueous solution, and a specific gravity of greater than, or about, 1. By varying the concentrations of the various agents, microspheres of uniform size ranging from 0.01 to 5 microns can be obtained with similar properties. On centrifuging at 30,000 g for more than 15 minutes, the microspheres are no longer suspendible in water, indicating loss of individual spheres through interconnection under such great pressure. Additionally, the microspheres according to the present invention are free of oil because no oils are used in their preparation, unlike the Widder et al. article cottonseed oil suspension method-produced microspheres described above, which are larger, less pure and less uniformly sized.

EXAMPLE 6

To one part by volume of an aqueous medium comprising 1 mM $K_2HPO_4$ at about 25 degrees Celsius in a suitable vessel, there was added bovine serum albumin to an initial concentration of 80 mg/ml. One part by volume of glutaraldehyde, pre-dissolved in another portion of the aqueous medium (0.16% v/v), was added with gentle stirring. Two parts of sodium dodecyl sulfate, pre-dissolved in a portion of the aqueous medium (8 mg/ml), were added with gentle stirring.

Prior to addition of the ethanol, 0.48 part of an adriamycin solution (5 mg/ml water) was added, with stirring. Instead of the adriamycin added, 0.48 parts of daunomycin (5 mg/ml water) or 0.48 parts of $Fe_3O_4$ (4% v/v suspension) can be added. In any case, four parts of ethanol/propanol (95/5) was added rapidly with gentle stirring. On standing, microspheres appear as a cloudy suspension. Chill the suspension to 4 degrees Celsius and let stand overnight. The microspheres can be centrifuged and washed with any desirable aqueous medium, or the microsphere suspension can be dialyzed against normal saline, to remove alcohol. Typically, the microspheres prepared thusly will contain about 2-3% by weight of adriamycin, daunomycin, or about 0.5 to 0.7% (weight per mg weight of albumin microspheres) of magnetite.

EXAMPLE 7

Wash the product of Example 5 with saline. Add 0.4 mg immunoglobulin/ml of microsphere suspension. Add 0.1 ml of 0.6% glutaraldehyde in aqueous medium and allow to react for 30 minutes; centrifuge spheres at 30,000 g for 2 min. and wash with saline. Suspend microspheres in saline. The product, immunoglobulin covalently bonded to the surface of the protein microsphere, is ready for use as a visual marker for antigenic sites on cell surfaces.

EXAMPLE 8

The following Examples were conducted to test the tolerance of mice for a potentially lethal dose of adriamycin in various forms of preparations, illustrating the effectiveness of the invention microspheres and method in improving the usefulness of adriamycin, for example, by limiting exposure of the host, except in targeted areas, where the increased phagocytotic activity or increased antigenic concentrations accompanying a cancerous site will increase targeted dosage of adriamycin at the affected site, in preference to all other areas of the body.

A: Microsphere Encapsulated Adriamycin

Adriamycin purchased from Sigma Chemical Company was encapsuled in bovine serum albumin in accordance with Example 4, experiment 5 (with initial concentration of HSA equal to 80 mg/ml). The suspension was extensively dialyzed overnight against four changes of a 400 fold by volume of normal saline to remove excess surfactant and alcohol and to raise the osmolarity of the suspension to that of normal saline. This preparation contains 0.25 mg adriamycin encapsuled in 8.3 mg protein microspheres per ml saline suspension.

B: Control: Soluble Adriamycin

A second preparation was produced by dissolving 0.25 mg of adriamycin in 1 ml of normal saline.

C: Control: "Blank" Protein Spheres

Control preparation comprising protein microspheres without adriamycin, made in accordance with Example 1, and suspended in normal saline at 8.3 mg per ml.

Procedure

Healthy male Balb/c mice (15 to 17 gm) were warmed with a 100 watt light bulb directed at them for 113 minutes to cause vasodilation of the tail veins. The tail was flexed slightly and 0.3 ml of preparation A, B or C was injected carefully into each mouse with a 27 gauge half-inch needle. For each example preparation and control preparation four mice were used. After the initial intravenous injection, on Day 0, all mice looked healthy. Similar injections were repeated on Day 3. One mouse injected with a total dose of 0.15 mg of soluble adriamycin died on Day 6. A third injection was performed on Day 7 at which point the remaining three mice injected with soluble adriamycin here too weak to attempt to fight the injection. All other mice, injected with encapsulated adriamycin or with Control protein microspheres, fought vigorously as usual inside the restrainer from which their tails were pulled for the injections. Two more mice injected with soluble adriamycin died on Day 13 or 14. The last mouse injected with soluble adriamycin survived as long as the remaining 8 mice injected with encapsulated adriamycin or "blank" spheres. However, this last mouse lost its tail eventually, due to atrophy of the tail, an obvious sign that adriamycin had been injected partially to the tail muscle, instead of being made available, for example, to the heart, resulting in cardiotoxicity, the usual cause of death. All other mice looked normal and healthy until sacrificed on Day 45.

It is thus demonstrated that adriamycin encapsulated in protein microspheres is less toxic than freely soluble adriamycin injected intravenously, which has been the normal route of administration in human patients with cancer, despite its dangers. With the present invention, however, the former problem of soluble adriamycin causing irreversible and cumulative cardiac damage is avoided since when encapsulated as described herein, the same amount of adriamycin now in the interior of spheres has much reduced and only partial exposure to the body fluids and tissues. The Control C shows that "blank" protein spheres are not toxic to mice.

The results obtained here with soluble adriamycin, in which an average of 14 mg of adriamycin injected per kg, i.v. killed three-fourths of the mice, is consistent with published results (Merck's Index) that the LD50 in mice i.v., of adriamycin is 20.8 mg/kg.

EXAMPLE 9

That the effectiveness of the biomodifying agent adriamycin is not lost while the protein microsphere protects the host is demonstrated as follows, on mice previously injected with tumors.

Eight healthy male Balb/c mice were primed by intra peritoneal injection of 0.5 ml of 2,6,10,14-Tetramethyl pentadecane, an adjuvant purchased from Aldrich Chemical Company, 7 days earlier. On Day 0, $2.5 \times 10^6$ myeloma cells, extracted immediately before from a mouse carrying the tumor, were injected into each of eight mice in a total volume of 0.25 ml. On Day 1, two mice were injected intraperitoneally with two ml of each of the following preparations: (a) saline, (b) "blank" protein spheres suspended at 4.2 mg per ml in normal saline, (c) protein microspheres with encapsulated adriamycin suspended at 4.2 mg protein microsphere containing 0.125 mg adriamycin in each ml of suspension in normal saline, and (d) soluble adriamycin, 0.125 mg per ml in saline. The injections were repeated on Day 4. The number of days of survival of mice was as follows: mice injected with preparation (a) (saline only): 11, 12 days; (b) "blank" protein microspheres: 11, 11 days; (c) adriamycin encapsulated in protein microspheres: 31, 35 days; and (d) soluble adriamycin: 30, 31 days. This demonstrates that the therapeutic effect of adriamycin encapsulated in protein spheres is not diminished compared to non-encapsulated soluble adriamycin. Therefore, the claimed microspheres provide at least the same amount of protection to the host in terms of killing a similar (but not the entire) amount of cancer cells in the host on injection of the drug in encapsulated form as compared to the soluble form.

EXAMPLE 10

Example 9 was repeated using as the biomodifying agent an antimetabolite selected from methotrexate, 6-mercaptopurine, cytosine arabinoside, or 5-fluorocil. Results are believed to be equivalent to the results in Example 9.

EXAMPLE 11

Example 9 was repeated using as the biomodifying agent an antibiotic other than adriamycin, namely daunomycin and actinomycin-D. Results are believed to be equivalent to the results in Example 9.

EXAMPLE 12

Preparation of Fluorescent Microspheres with Immunoglobulin Coated on the Surface (Immunomicrospheres)

1. Prepare fluorescent albumin molecules (f)BSA, by conjugation of 2 mg of Fluorescene Isothiocyanate (FITC) with 300 mg of BSA in a very basic buffer (3.7 g of sodium bicarbonate and 0.6 g of sodium carbonate per 100 ml of water). Separate the fluorescent albumin from unreacted FITC over a column chromatography.

2. Mix 0.3 ml of the above (f) BSA with 1.2 ml of an 80 mg/ml unlabeled BSA solution. Then, mix in 1.5 ml of a 0.16% GL ml solution. After 10 minutes in room temperature, add 1.2 ml of SDS (9 mg/ml). After another 5 minutes, add 8 ml of ETOH (100%). Yellowish fluorescent microspheres were formed. Wash microspheres 3 times with saline.

3. Conjugate Sheep-anti-Rabbit Antibody (SR) to above microspheres by adding 2 mg of SR in 0.1 ml buffer to 4.5 ml of microsphere suspension. Then, add 0.3 ml of a 1% GL solution to the total of 4.6 ml mixture. After one hour of reaction in room temperature, the spheres were washed twice in saline to remove excess SAR.

4. Preparation of chicken red blood cells (cRBC) with special surface markers or antigens (rabbit anti-chicken antibodies =RAC): Sensitize cRBCs by (a) washing 0.5 ml of whole cRBC suspension in normal saline twice, (b) mix with 1 ml of a 1/200 dilution of commercially purchased RAC, (c) allow immunoreaction to complete in half an hour at room temperature, (d) wash off excess RAC.

5. Labeling of cRBC with immunomicrospheres: add 0.1 ml of the above prepared fluorescent SR immunospheres to 1 ml of the sensitized cRBC suspension. Incubate for 15 minutes in room temperature. Examination under fluorescence equipped microscope showed all sensitized cRBCs become fluorescent due to the attached fluorescent microspheres.

6. Similar treatment of non-sensitized cRBC (i.e. those without added Rabbit markers on the cRBC) resulted in no fluorescence on the cells.

EXAMPLE 13

Example 12 repeated using as the biomodifying agent an oxide, chloride or sulfide of a metal such as $Fe_3O_4$, or $ErCl_3$. Results are equivalent. The incorporation of these compounds enables magnetic field manipulation of the microspheres, controlling their application to different parts of the body by external application of the field, and thus the targeting of treatment.

As will be evident from the foregoing, the microspheres herein can contain numerous different agents, solely, or in myriad combinations, e.g. daunomycin incorporated in the microsphere, with magnetite particles, whereby the therapeutic effect of the daunomycin can be externally targeted. The further incorporation or attachment of a radioisotope, or a tracer dye, enables detection of the exact situs of treatment.

EXAMPLE 14

Experiment to Demonstrate Activity of an Enzyme After Covalent Bonding to the Surface of Albumin Microspheres 1. The enzyme system involves the enzyme Alkaline phosphatase (APT) which will degrade the colorless substrate p-Nitrophenyl phosphate (PNPP) in a suitable alkaline buffer solution. The degradation process will result in a yellowish end product. Measurement of the concentration of the yellowish product provides an index of the activity of APT.

2. Preparation of the enzyme-microsphere conjugate: Dissolve 2 mg of APT in 2.2 ml of a sodium phosphate buffer pH 7.6, containing 10 mg of albumin microsphere suspension. Add 0.2 ml of a 0.72% glutaraldehyde solution to cross-link APT to the microspheres. Incubate the mixture at room temperature for 40 minutes. Centrifuge the microspheres and discard the supernatant containing the unreacted APT and residual glutaraldehyde. Wash the enzyme-microsphere conjugates twice more in normal saline and finally re-suspend the conjugates in normal saline.

3. Testing activity of APT which is covalently bonded to the surface of microspheres: Dissolve PNPP in a carbonate/bicarbonate buffer pH 10.2 to result in a 1 mg PNPP/ ml buffer concentration. Mixing 0.5 ml of the enzyme microsphere conjugate suspension with 0.5 ml of the substrate PNPP solution resulted in the immediate appearance of a yellowish solution, indicative that the enzymes were still highly active after the conjugation process. As a control, mix 0.5 ml of the last normal saline supernatant (with microspheres completely removed from it) with 0.5 ml of the PNPP solution. The mixture remained colorless and clear, indicating that it contained no APT enzymes. Therefore, the yellowish compound observed in the enzyme-microsphere conjugation preparation was not due to excessive unbonded APT left over in a soluble dorm from inadequate washing of the conjugation preparation, but rather due to APT covalently bonded to the protein microspheres.

4. The significance of this experiment is that it demonstrates that enzymes can remain active even on the surface (or perhaps even the interior) of a microsphere, as compared to a soluble state. Therefore, in conditions where high concentrations of enzymes are needed such as the use of L-asparaginase against certain cancer cells, a higher local concentration can be achieved by attaching multiple enzyme molecules (or even a cascade of enzyme systems with synergistic effects) on the surface of a microsphere. In addition, the microsphere will allow a targeting capacity either by the presence of magnetic particles inside the spheres or by immunoglobulins on their surface to recognize the target cells. Such are some examples of the efficacy of active enzyme-microsphere conjugates over simple enzyme solutions.

I claim:

1. A process for manufacturing protein microspheres, comprising:
    a) dissolving protein molecules in an aqueous buffer solution to form a protein solution;
    b) adding a surfactant;
    c) adding a desolvating agent to the admixture of protein solution and surfactant to produce a turbid mixture comprising substantially monodispersed protein microspheres; and
    d) adding a cross-linking agent to the turbid mixture formed in step c).

2. The process described in claim 1 wherein said protein molecules have at least one biological element attached thereto.

3. The process described in claim 1 additionally comprising adding at least one biological element to said protein solution prior to adding said desolvating agent.

4. The process described in claim 1 additionally comprising adding at least one biological element to said turbid mixture prior to adding said cross-linking agent and resulting in attachment of biological element to said protein microspheres.

5. The process described in claim 1 additionally comprising adding at least one biological element subsequent to the addition of said cross-linking agent and resulting in attachment of biological element to said protein microspheres.

6. The process described in claims 2, 3, 4 or 5 wherein the biological element is chosen from the group consisting of the following: alkaloids, amino acids, antibiotics, carbohydrates, carcinogens, immunoglobulins or globulins, halogenated compounds, hormones, lipids, nucleotides, polypeptides, porphyrins, steroids, vitamins, lecithins, metal sulfides, metal halides, metal oxides, antifungal compounds, enzymes, and chemotherapeutic agents.

7. The process described in claim 1 wherein said protein molecules are chosen from any one or more of the group consisting of albumin, collagen, hemoglobin, and immunoglobulin.

8. The process described in claim 7 wherein the concentration of protein molecules just prior to the addition of desolvating agent is within the range of approximately 0.225–62.50 mg/ml.

9. The process described in claim 7 wherein said protein molecules comprise albumin.

10. The process described in claim 9 wherein the concentration of albumin just prior to the addition of desolvating agent is within the range of approximately 9.00–20.00 mg/ml.

11. The process described in claim 10 wherein the concentration of albumin just prior to the addition of desolvating agent is 15 mg/ml within an accuracy of plus or minus 10%.

12. The process described in claim 7 wherein said protein molecules are hemoglobin.

13. The process described in claim 12 wherein the concentration of hemoglobin just prior to the addition of desolvating agent is 3.7 mg/ml within an accuracy of plus or minus 20%.

14. The process described in claim 1 wherein said aqueous buffer solution is maintained between 0 and 42 degrees Centigrade.

15. The process described in claim 1 wherein the pH of said aqueous buffer solution is maintained between 5 and 9.

16. The process described in claim 1 wherein the concentration of said surfactant is approximately 0.1 to 50 mg/ml of said aqueous buffer solution.

17. The process described in claim 11 wherein said surfactant is a detergent.

18. The process described in claim 1 wherein said surfactant is sodium lauryl sulfate.

19. The process described in claim 1 wherein said desolvating agent is an alcohol.

20. The process described in claim 19 wherein said alcohol is chosen from the group consisting of methanol, ethanol, propanol, and butanol.

21. The process described in claim 11 wherein said cross-linking agent is a polyaldehyde which is added in an amount in the range of 0.002 to 10.0 volume per 100 volume of said aqueous buffer solution.

22. The process described in claim 21 wherein polyaldehyde is selected from the group consisting of glutaraldehyde, polyglutaraldehyde, and polyacrotein.

23. The process described in claim 1 additionally comprising the step of removing said desolvating agent and other unreacted or partially-reacted soluble material from said protein microspheres.

24. The process described in claim 23 wherein said step of removing desolvating agent is chosen from one or more of the following methods: dialysis, centrifugation and washing, gradient centrifugation, gel-filtration, electrophoresis, column chromatography, gradient centrifugation, thin-layer chromatography, hollow-fiber ultrafiltration, and tangential filtration.

* * * * *

UNITED STATES PATENT AND TRADEMARK OFFICE
CERTIFICATE OF CORRECTION

PATENT NO. : 5,069,936
DATED : December 3, 1991
INVENTOR(S) : Richard C. K. Yen

It is certified that error appears in the above-identified patent and that said Letters Patent is hereby corrected as shown below:

Column 34, line 38, change "11" to --1--.

Column 34, line 47, change "11" to --1--.

Signed and Sealed this

Eighteenth Day of May, 1993

Attest:

MICHAEL K. KIRK

Attesting Officer    Acting Commissioner of Patents and Trademarks